United States Patent [19]

Sørensen et al.

[11] 4,151,108

[45] Apr. 24, 1979

[54] REFERENCE LIQUID FOR BLOOD GAS EQUIPMENT

[75] Inventors: Soren K. Sørensen, Glostrup; Carl C. Holbek, Allerød, both of Denmark

[73] Assignee: Radiometer A/S, Copenhagen, Denmark

[21] Appl. No.: 806,837

[22] Filed: Jun. 15, 1977

Related U.S. Application Data

[63] Continuation-in-part of Ser. No. 652,817, Jan. 27, 1976, abandoned.

[30] Foreign Application Priority Data

Jun. 17, 1976 [DK] Denmark .................... 2724/76

[51] Int. Cl.² .................................................. C09K 3/00
[52] U.S. Cl. ............................ 252/408; 23/230 B; 252/312; 252/316
[58] Field of Search .............. 252/316, 312, 408; 260/2.5 S, 2.5 L, 2.5 M; 23/230 B

[56] References Cited

U.S. PATENT DOCUMENTS

| | | | |
|---|---|---|---|
| 3,380,929 | 4/1968 | Petersen | 252/408 |
| 3,429,827 | 2/1969 | Ruus | 252/316 |
| 3,639,498 | 2/1972 | Vlismas | 260/2.5 S |
| 3,681,255 | 8/1972 | Wilfore | 252/408 R |
| 3,686,701 | 8/1972 | Charle et al. | 252/316 |
| 3,778,381 | 12/1973 | Rosano et al. | 252/312 |
| 3,778,383 | 12/1973 | Schibler et al. | 252/316 |
| 3,796,669 | 3/1974 | Kiritani et al. | 252/316 |
| 3,823,091 | 7/1974 | Samejima et al. | 252/312 |
| 3,843,557 | 10/1974 | Fanger et al. | 252/316 |
| 3,859,049 | 1/1975 | Ware | 252/408 R |
| 3,864,084 | 2/1975 | Folkman | 23/230 B |
| 3,872,023 | 3/1975 | Baum et al. | 252/316 |
| 3,874,850 | 4/1975 | Sorensen et al. | 23/230 B |
| 3,993,581 | 11/1976 | Yokoyama et al. | 252/312 |
| 4,016,098 | 4/1977 | Saeki et al. | 252/316 |

FOREIGN PATENT DOCUMENTS

| | | | |
|---|---|---|---|
| 2253050 | 5/1973 | Fed. Rep. of Germany | 252/316 |
| 2236909 | 2/1974 | Fed. Rep. of Germany | 252/408 R |
| 1343870 | 1/1974 | United Kingdom | 252/408 R |

OTHER PUBLICATIONS

Clark, Jr., L. et al., Ala. J. Med. Sci., vol. 9, No. 1, pp. 16–29, (1972).

*Primary Examiner*—Benjamin R. Padgett
*Assistant Examiner*—T. S. Gron
*Attorney, Agent, or Firm*—Hubbell, Cohen, Stiefel & Gross

[57] ABSTRACT

A reference liquid for the calibration and/or quality control of blood gas analyzers. The reference liquid comprises an aqueous phase and either polymer-coated microcapsules containing at least one organic substance functioning as oxygen carrier, or porous particles of a solid substance functioning as oxygen carrier. An example of the polymer-coated microcapsules is nylon-coated microcapsules containing a mixture of perfluorotributyl amine and isooctane. An example of the porous particles of a solid substance is particles of porous silicone rubber.

12 Claims, 3 Drawing Figures

Fig.1

REFERENCE LIQUID FOR BLOOD GAS EQUIPMENT

CROSS-REFERENCE TO RELATED APPLICATION

This application is a continuation-in-part of application Ser. No. 652,817, filed Jan. 27, 1976, now abandoned.

The present invention relates to a reference liquid for quality control and/or calibration of blood gas measuring equipment.

Blood gas measuring apparatuses are known which are designed for measuring, by means of suitable measuring electrodes, blood pH, concentration of dissolved carbon dioxide in blood, expressed as $P_{CO_2}$ (the partial pressure of carbon dioxide) and the concentration of dissolved oxygen in the blood, expressed as $P_{O_2}$ (the partial pressure of oxygen), and one known fully automatic blood gas measuring apparatus (Radiometer ABL1, described, e.g. in U.S. Pat. No. 3,874,850) also simultaneously measures the blood hemoglobin content (Hb) which is otherwise normally measured separately.

From these four central parameters may be calculated various derived parameters which are of great significance to the judgement of so-called acid-base status of the organism.

The measurements referred to above are all relative measurements where the unknown sample is compared with standards. Hence, the quality of these standards is decisive to the quality of the measurement of the single parameters.

When using manual or semiautomatic blood gas measuring equipment, great technical skill is nowadays a requirement to the user of the measuring equipment in order to obtain measurements of satisfactory quality. The technical level of the user may be lower when a fully automatic self-calibrating equipment is used, e.g. of the type described in the above-mentioned U.S. patent, but this does not remove the necessity or desirability of being able to check the measuring quality of the equipment, including the quality of the standards, calibration liquids, etc., of the equipment, using a known reference.

Even though it is, in principle, generally known to check a measuring equipment by introducing a sample of known properties into the equipment, this is a great problem in connection with equipment for measuring pH—$P_{CO_2}$—$P_{O_2}$— and optionally Hb.

A sample (a blood sample or another aqueous solution) of this type is normally not stable during any longer period ($CO_2$ and $O_2$ escape from the sample) which means that the sample must be prepared on the spot by the user. Normally, this gives rise to problems involving extraordinarily much labor, expensive extra equipment and uncertainty, as the preparation process is technically rather complicated.

All over the world, there is in our days an interest in a control system for measuring values from equipment of the type mentioned, as this equipment is used directly in connection with patient treatment and often under extremely critical circumstances (e.g. during surgery). In the U.S.A., Congress has dealt with this problem during recent years, and at present, the legislation tends toward requiring that the "supplier of blood data", e.g. the head doctor of the laboratory, shall be able to prove, at any time, that the measuring equipment used is able to yield reliable data in that it has been checked by means of a system independent of the normal calibration system of the equipment (quality control).

Hence, the general desire to-day (also outside the U.S.A.) is that one would be able to buy for this quality control, small containers with samples of known composition and of great reliability.

All blood gas measuring equipment commercially available requires frequent calibration, usually with intervals of some hours. For this purpose, the known art uses, for certain types of equipment, various calibration liquids, some of which (e.g. pH buffer mixtures) are commercially available in small containers and show high reliability with respect to keeping the stated pH values, whereas the calibration liquids for the calibration of other parts of the measuring equipment, e.g. the $P_{CO_2}$ measuring equipment and the $P_{O_2}$ measuring equipment, are at the moment not commercially available in suitable containers and with well-defined data, but will have to be prepared on the spot, which leads to the above problems. Some technically advanced blood gas measuring equipment, e.g. the above-mentioned fully automatic Radiometer ABL1 blood gas measuring equipment, use solutions which in the equipment proper are equilibrated with known gas mixtures to obtain well-defined values for pH, $P_{CO_2}$, and $P_{O_2}$, and the calibration liquids thus prepared in the equipment and showing well-defined data are used for the calibration within the equipment, without being transferred to separate containers.

It would be of high interest to be able to perform the very calibration of the blood gas measuring equipment, especially semiautomatic equipment, using a handy reference liquid which may be produced and packed in suitable unit portions and distributed and stored with retention of its relevant data with high exactitude and reliability, in order that the calibration of the blood gas measuring equipment can be performed simply by introducing a unit portion or a part thereof in the equipment without the necessity of any special preparation or checking of the liquid.

The present invention provides a reference liquid which may be used for quality control and/or calibration of blood gas measuring equipment, and which is known with respect to the parameters pH, $P_{CO_2}$, $P_{O_2}$, and, if desired, a parameter representing the hemoglobin concentration.

U.S. Pat. No. 3,681,255 and the specification of Danish patent application No. 1261/72 mention the possibility of using a single calibration liquid with known hydrogen carbonate ion concentration, known partial pressure of carbon dioxide (and consequently in accordance with the known Henderson-Hasselbalch equation, known pH) and known partial pressure of oxygen for calibration of the measuring electrodes in blood gas measuring equipment, and according to the above-mentioned U.S. patent specification, said calibration liquid may be delivered to the user in a gas-tight container.

Although calibration liquids of this type would, due to the inclusion in a gas-tight container with retention of the known parameters, in principle be suitable for quality control and calibration of blood gas measuring equipment, it is difficult in practice, using the known calibration liquids, in other words in the actual performance of the quality control or calibration by introducing the reference liquid into the blood gas measuring equipment, to fulfil such exactitude requirements which may reasonably be made on a reference liquid for calibration and quality control. Especially, the $P_{O_2}$ control involves serious difficulties, and with the known art calibration liquids contained in gas-tightly sealed containers, it is not possible to obtain any reliable control or calibration of the $P_{O_2}$ system under all circumstances.

The reference liquid according to the present invention is contained in a gas-tight container and shows, at a fixed temperature, a known pH; a known partial pressure of carbon dioxide and a known partial pressure of oxygen; and additionally comprises oxygen reversibly contained in a dispersed organic substance which is able to contain, per volume unit, a larger amount of oxygen than water can contain; and optionally a coloring component.

When the reference liquid according to the invention contains a coloring component, it may be used for quality control and/or calibration of the equipment with respect to the determination of the amount of hemoglobin, in addition to the quality control and/or calibration of the equipment with respect to the determination of pH, $P_{CO_2}$ and $P_{O_2}$.

In the reference liquid according to the invention, the problem of unsatisfactory reliability of the control or the calibration of the $P_{O_2}$ system is solved by having the liquid (which is usually an aqueous liquid) comprise oxygen reversibly contained in a dispersed organic substance which, per volume unit, is able to take up a larger amount of oxygen than is water, in order to increase the $O_2$ capacity. This results in an increased "oxygen buffer capacity", so that any loss or gain of oxygen which may arise during manipulation and measurement, will result in a relatively small change in the $P_{O_2}$ value of the solution, this being the parameter with respect to which the $P_{O_2}$ part of the equipment is to be checked and/or calibrated.

The term "dispersed organic substance" is intended to comprise both organic substance which is so finely dispersed that a genuine or colloidal solution of the organic substance in the (usually predominantly aqueous) liquid is obtained, and organic substance in emulsion or in suspension in the predominantly aqueous liquid. This meaning may also be expressed by the term "dispersed" covering, in the present context, the three concepts of "dissolved", "emulsified", and "suspended".

The term "reversibly contained" is intended to describe that the oxygen is present in the organic substance in such a manner that the organic substance is able to deliver or take up oxygen under the manipulation and measuring conditions, so that the organic substance will, due to its ability to contain larger amounts of oxygen per volume unit than water, increase the oxygen buffer capacity of the reference liquid. The term "reversibly contained" may comprise both such cases in which the oxygen is dissolved or otherwise predominantly physically bound in the organic substance, and such cases where the oxygen is predominantly chemically bound, especially complex bound, to or in the organic substance in question.

Non-water soluble organic materials showing a great solution power for oxygen, are e.g. oils or oily synthetic organic substances and organic polymers. As examples may be mentioned hydrocarbons such as isooctane, silicone oils and silicon rubbers and fluorocarbon compounds, i.e. fluorinated, especially perfluorinated, hydrocarbons and compounds containing such fluorinated hydrocarbon groups, as well as polymers thereof. With such non-water soluble organic materials which are liquids of lipoid character or solid substances, dispersions may be prepared which are emulsions of lipoid-in-water-type or suspensions. For the purpose of the present invention, such systems show the advantage that the great oxygen-soluting power of the lipoids or solids results in a large oxygen buffer capacity, whereas the liquid still retains its property as aqueous solution and hence, continuously permits the establishment of a $P_{CO_2}$/pH buffer system. Hence, expecially preferred reference liquids according to the invention contain oxygen dissolved in emulsified or suspended non-water soluble organic substances. Of course, it is also possible to use combinations of water soluble and non-water soluble organic substances with large capacity for taking up oxygen.

Quite generally, the following criteria should apply to the selection of the non-water soluble organic substance used as an oxygen carrier:

1. The oxygen carrier should have high soluting power for oxygen (reversible).
2. The oxygen carrier should show no (or little) protolytical activity.
3. The organic phase consisting of the oxygen carrier should be dispersible in an aqueous buffer to fulfil the following requirements:
    (a) High concentration of organic phase (which give a high $O_2$ capacity of the mixture).
    (b) The mixture should be stable.
    (c) The density of the mixture should be less than or equal to the density of blood, on account of blood gas measuring equipment containing salt bridges, the use of which is dependent on the blood having a smaller density than the salt solution.
    (d) The viscosity of the mixture should not be too high.
4. The oxygen carrier should be extensively chemically inert (in order to not destroy the structural materials in the blood gas measuring equipment).
5. The oxygen carrier should preferably be undangerous to handle, and
6. the oxygen carrier should preferably be a commercially available material and, hence, cheap and easy to obtain.

As an illustration of the increase in solubility for oxygen which is obtained by using one of the substances mentioned, water soluble or non-water soluble, it may be mentioned that the solubility of $O_2$ (at 1 atmosphere's oxygen pressure and 25° C.) in water is 2.4% v/v, while it is 12% v/v in olive oil, typically 50% v/v in fluorocarbon compounds, typically 18% v/v in silicone rubbers, typically 20% v/v in silicone oils, and about 36% v/v in isooctane.

Figure 1:
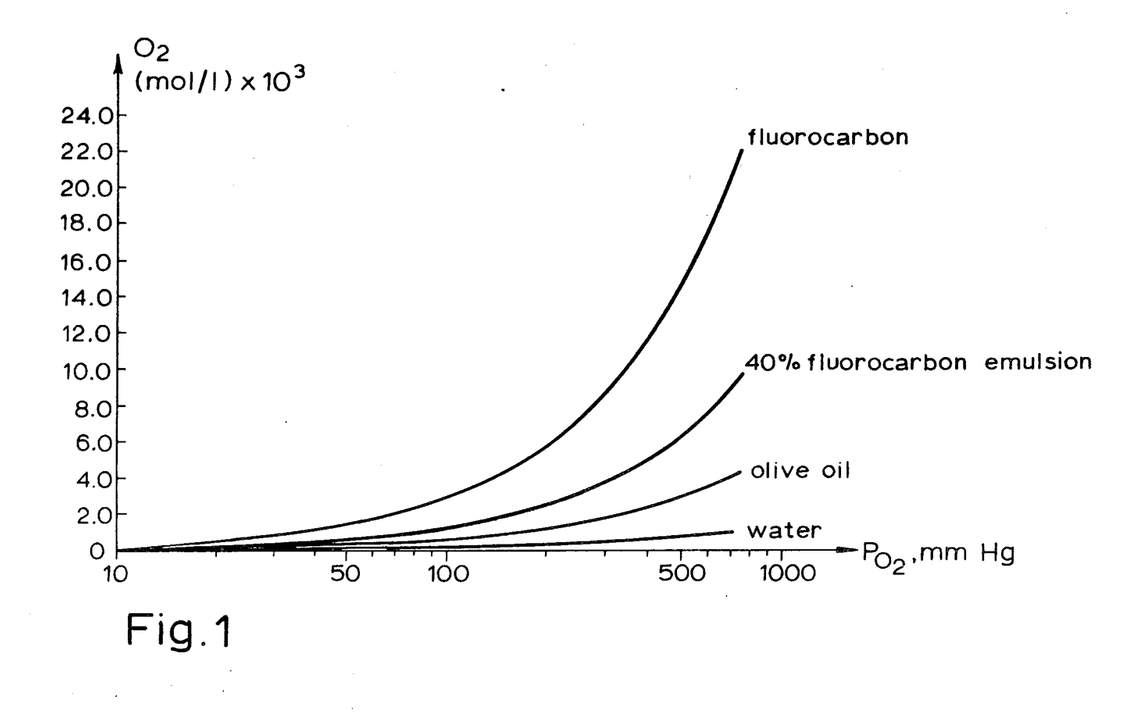
FIG. 1 is a graphical representation showing the molar amount of dissolved oxygen as a function of the partial pressure of oxygen for a number of reference liquids according to the invention.

The amount of dissolved oxygen in various systems as functions of the partial pressure of oxygen (single logarithmical plot) is shown in FIG. 1 in which "fluorocarbon" designates perfluorotributylamine. It will be noted that while even a very small change in the oxygen amount in pure water will result in a very large difference in $P_{O_2}$, a change of the oxygen amount in, e.g., the fluorocarbon compound will result in a far smaller change in $P_{O_2}$, and that, e.g., a 40% emulsion of the fluorocarbon compound in water shows a far better oxygen buffer capacity than water, i.e., shows far less $P_{O_2}$ change at a given change in oxygen content.

When the reference liquid according to the invention is an emulsion or suspension, it is preferred that the emulsified or suspended phase constitutes at the most 80% of the total volume, especially 40-70%, as the water phase should of course be of a sufficient proportion so as to avoid a decrease in the quality of the pH measurement. Hence, it is clear that in composing the liquid according to the invention, one will preferably choose such emulsified or suspended components which show an especially high solubility for oxygen, e.g. the above-mentioned fluorocarbon compounds.

As examples of fluorohydrocarbons and fluorohydrocarbon group-containing compounds, in other words fluorocarbon compounds, which are useful for the purpose of the present invention may be mentioned perfluorotributyl amine $((C_4F_9)_3N)$ which is sold by 3M Company under the designation "FC 43", perfluoromethyl cyclohexane and perfluorodimethyl decaline.

Because of its good emulsifying properties and high ability of dissolving oxygen, perfluorotributyl amine is a preferred compound. As an example of a silicone oil useful as emulsified phase in the reference liquid according to the invention may be mentioned Dow Corning "200 Silicone Oil", and as an example of a silicon rubber useful as suspended phase in the reference liquid according to the invention may be mentioned silicone rubber CAF4/60 Rhodorsil, Rhône Poulenc, Paris.

According to a particular aspect of the present invention, a suspended solid is used which is porous and which may, in its porosities, contain oxygen or an oxygen-containing gas, and a suitable material for this purpose is porous silicone rubber. Porous silicone rubber useful for this purpose may, for example, be prepared by applying, prior to and/or during the curing of the silicone rubber, a superatmospheric pressure which is thereafter released during the curing. Porous silicone rubber useful for this purpose may also be prepared by dispersing in the silicone rubber, prior to the curing, a volatile non-solvent for silicone rubber, for example methanol, and thereafter curing the silicone rubber and evaporating the volatile substance.

To obtain a stable emulsion or suspension it may be necessary that the reference liquid according to the invention contains a suitable emulsifying or suspending agent, and this agent may be of any type which does not adversely influence the parameters to be determined by means of the reference liquid, and which gives a stable emulsion or suspension of the organic material selected. Suitable emulsifiers or suspending agents for this purpose are commercially available. As an example of an emulsifier which has been found to be suitable in the preparation of emulsions of fluorohydrocarbons in water for the purpose of the present invention may be mentioned Pluriol PE 6800, BASF (polyoxy propylene polyoxy ethylene).

As mentioned above, the organic substance in which the oxygen in the reference liquid according to the invention is reversibly contained may be a substance to which oxygen is reversibly chemically bound, especially complex-bound.

Most chemical processes involving oxygen are characteristic in that the processes are substantially irreversible, so that an oxygen-containing compound once formed will not to any substantial degree be able to liberate oxygen or, expressed in another manner, the oxygen-containing compounds formed by the irreversible processes are not suitable for increasing the oxygen buffer capacity of the reference liquids according to the present invention.

However, reversible oxygen processes do exist, e.g. in the blood hemoglobin molecule, which is able to reversibly take up and give off oxygen in substantial amounts, and which therefore in principle would be excellently suitable for the purpose of the present invention. However, outside the organism, the hemoglobin molecule, like other biological substances such as proteins or proteinaceous complexes, is relatively unstable, and reference liquids prepared with hemoglobin or other biological substances like proteins or proteinaceous complexes as oxygen capacity-increasing organic substance will, therefore, show the disadvantage that they are stable only for relatively short periods unless special precautions are taken to secure their stability, e.g. freezing of the reference liquid immediately or shortly after its preparation and packing, distribution and storing of the reference liquid in frozen form, addition of suitable stabilizers to prevent chemical degradation and suitable sterilization or addition of antibiotics to prevent microbial degradation.

However, other—and simpler and less sensible—organic compounds than the hemoglobin molecule are known which are able to reversibly complex-bind oxygen. As examples of such non-biological compounds may especially be mentioned metal organic compounds of transition group metals, especially cobalt or iron, in which the metal is bound, usually complex-bound, to nitrogen-containing groups, e.g. transition group metal complexes with porfyrine-like compounds such as iron-(II)phthalocyanine tetrasulfonic acid.

For the purpose of the present invention, the organic substance which is able to chemically bind, especially complex-bind, oxygen reversibly should preferably be one which has a suitable position of the equilibrium of the reversible oxygen reaction in question, i.e. a position of the equilibrium which resembles that of hemoglobin (the greatest resemblance with authentic blood), and/or a position of the equilibrium which results in an optimum oxygen buffer capacity at or about the $P_{O_2}$ value which is to be possessed by the reference liquid.

With respect to the position of the equilibrium of the oxygen reaction of hemoglobin, the following applies when the oxygen uptake of the blood is considered in a simplified manner:

$$Hb + O_2 \rightleftharpoons HbO_2$$

wherein Hb is the hemoglobin molecule, $O_2$ is the oxygen molecule, and $HbO_2$ is the oxygen-containing hemoglobin complex.

The solubility of oxygen (in free form) in the water phase of blood can reasonably be put at $1.4 \cdot 10^{-6}$ mole of oxygen per liter per mm Hg oxygen partial pressure. Empirically, at an oxygen partial pressure of 27 mm Hg, equal amounts of on the one hand hemoglobin on the Hb form and on the other hand hemoglobin on $HbO_2$ form are present in the blood. At this partial pressure, the concentration of dissolved oxygen in the water phase of blood is:

$$[O_2] = 1.4 \cdot 10^{-6} \cdot 27 \sim 3.8 \cdot 10^{-5}.$$

The stability constant K for the oxygen-containing hemoglobin complex is $$K = \frac{[HbO_2]}{[Hb][O_2]}$$

and as (vide above) $[HbO_2]=[Hb]$ at $[O_2] \sim 3.8 \cdot 10^{-5}$, the following applies:

$$K = \frac{1}{3.8 \cdot 10^{-5}} \sim K = 10^{4.5}$$

From this follows that among the oxygen complex-forming organic compounds binding oxygen in the same manner as hemoglobin, i.e. according to the above reaction scheme, the ideal compounds for use as oxygen buffers in a reference liquid which is very close to the properties of blood in this regard will be such compounds, for which the stability constant of their oxygen complex is about $10^{4.5}$, e.g. in the range of $10^3-10^{5.5}$, especially $10^4-10^5$.

Another type of (different from hemoglobin) organic compounds which reversibly form complex with oxygen, bind oxygen according to the reaction scheme:

$$2L + O_2 \rightleftharpoons L-O_2-L$$

wherein L is the ligand which is able to bind oxygen, and $L-O_2-L$ is the complex compound in its oxygenated form.

The stability constant of the above-mentioned oxygenated complex compound $L-O_2-L$ is $$K = \frac{[L-O_2-L]}{[L]^2[O_2]}$$

wherein $[O_2]$ is the concentration of oxygen (in free form) dissolved in the system in question. Like the above calculated stability constant for the oxygenated hemoglobin complex, this constant is, to some extent, temperature dependent; however, for the purpose of the present invention, this temperature dependency can usually be disregarded. When the concentration of L is designated $\alpha$, and the concentration of $L-O_2-L$ is designated $\beta$, $\alpha + 2\beta = c$ (cf. the reaction scheme), or $\alpha = c - 2\beta$, c being the total concentration of the ligand. From this follows:

$$\frac{\beta}{\alpha^2[O_2]} = K = \frac{\beta}{(c-2\beta)^2[O_2]}$$

$$\beta = K(c-2\beta)^2[O_2] \quad (c-2\beta)^2 = c^2 + 4\beta^2 - 4c\beta$$

$$\beta = K[O_2]c^2 + 4K[O_2]\beta^2 - 4K[O_2]c\beta$$

$$4K[O_2]\beta^2 - 4K[O_2]c\beta - \beta + K[O_2]c^2 = 0$$

$$4K[O_2]\beta^2 - (4K[O_2]c + 1)\beta + K[O_2]c^2 = 0$$

$$\beta = \frac{(4K[O_2]c + 1)^{(\pm)}\sqrt{(4K[O_2]c + 1)^2 - 16K[O_2]K[O_2]c^2}}{8K[O_2]}$$

wherein $\beta$, as appears from the above, represents the concentration of complex-bound oxygen.

The total oxygen concentration in complex systems, $TO_2$, is $$TO_2 = [O_2] + \beta$$

wherein $[O_2]$ is the concentration of dissolved oxygen, and $\beta$ is the concentration of complex-bound oxygen.

Decisive to the suitability of the oxygen complex-forming compound for use in the liquid according to the invention is that around the oxygen partial pressure which the reference liquid is to possess, a suitable oxygen buffer capacity should be obtained, which means that any loss of small amounts of oxygen from the liquid, or any gain of small amounts of oxygen to the liquid, e.g. during the manipulation of the liquid and during a calibration operation, should result in as small a change in the $P_{O_2}$ of the liquid as possible. A high oxygen buffer capacity is of course in principle obtained when the concentration of the oxygen complex-forming compound in the reference liquid is high, but the oxygen partial pressure around which the buffer effect has its optimum depends on both the concentration mentioned and on the size of the above-mentioned stability constant K. When composing a reference liquid according to the invention using an oxygen complex-forming compound, one should, therefore, as oxygen complex-forming compound preferably select such compound in such concentration that optimum oxygen buffer capacity is obtained around the oxygen partial pressure to be possessed by the reference liquid. In practice, the oxygen buffer capacity for the above-mentioned complex system can be defined as $$d\beta/(d\log[O_2])$$

wherein $\beta$ and $[O_2]$ are as defined above, and hence, the maximum oxygen buffer capacity is the one at which $$\frac{d^2\beta}{d(\log[O_2])^2} = 0,$$

which for this function is synonymous with $$\frac{d^2\log[O_2]}{d\beta^2} = 0.$$

As $= K$ it follows that $[O_2] = \dfrac{\beta}{K(c-2\beta)^2}$ $\log[O_2] = -\log K + \log\beta - 2\log(c-2\beta)$ $$\frac{d\log[O_2]}{d(c-2\beta)} \cdot \frac{d(c-2\beta)}{d\beta} = \frac{d\log[O_2]}{d\beta}$$

$$\frac{d\log[O_2]}{d\beta} = \frac{1}{\beta}(\log e) - 2\frac{1}{c-2\beta}\log e(-2)$$

$$\frac{d\log[O_2]}{d\beta} = \log e\left(\frac{1}{\beta} + \frac{4}{c-2\beta}\right)$$

$$\frac{d^2\log[O_2]}{d\beta^2} = \frac{-\log e}{\beta^2} + \log e(-4(c-2\beta)^{-2}(-2))$$

$$\frac{d^2\log[O_2]}{d\beta^2} = \log e\left[\frac{8}{(c-2\beta)^2} - \frac{1}{\beta^2}\right]$$

From this follows that $$\frac{d^2\log[O_2]}{d\beta^2} = 0 \text{ for}$$

$$\frac{8}{(c-2\beta)^2} = \frac{1}{\beta^2}$$

$8\beta^2 = (c-2\beta)^2 = c^2 + 4\beta^2 - 4c\beta$ $4\beta^2 + 4c\beta - c^2 = 0$ $$\beta = \frac{-4c \pm \sqrt{16c^2 + 16c^2}}{8} = \frac{-4c(\pm)4c\sqrt{2}}{8}$$

$$\beta = \frac{4c(\sqrt{2}-1)}{8} = \frac{c(\sqrt{2}-1)}{2} = 0{,}207 \cdot c$$

On this basis, there may be calculated, as examples, suitable stability constants for oxygen complexes for use in reference liquids, the oxygen partial pressure of which is to be at one of the three values at which it is often desired to calibrate, i.e. 500 mm Hg, 150 mm Hg, and 50 mm Hg. For these, the following is true:

(1) $[O_2] = 6 \cdot 10^{-4}$ mol/liter ($\sim 500$ mm Hg)
(2) $[O_2] = 2 \cdot 10^{-4}$ mol/liter ($\sim 150$ mm Hg)
(3) $[O_2] = 6 \cdot 10^{-5}$ mol/liter ($\sim 50$ mm Hg)

If it is desired to use the ligand in these cases in a concentration of $10^{-1}$ mol/liter, the following values are calculated for the stability constant K which at the three [O₂] values mentioned gives maximum oxygen buffer capacity:

$$K = \frac{\beta}{[c - 2\beta]^2 [O_2]} \text{ (cf. above)}$$

$$K = \frac{0.207 \cdot c}{(c - 2 \cdot 0.207 \cdot c)^2 [O_2]} = \frac{0.207 \cdot c}{(0.586 \cdot c)^2 [O_2]}$$

$$K = \frac{0.603}{c \cdot [O_2]}$$

$$K_1 = \frac{0.603}{10^{-1} \cdot 6 \cdot 10^{-4}} = 10^4$$

$$K_2 = \frac{0.603}{10^{-1} \cdot 2 \cdot 10^{-4}} = 3 \times 10^4$$

$$K_3 = \frac{0.603}{10^{-1} \cdot 6 \cdot 10^{-5}} = 10^5$$

Figure 2:
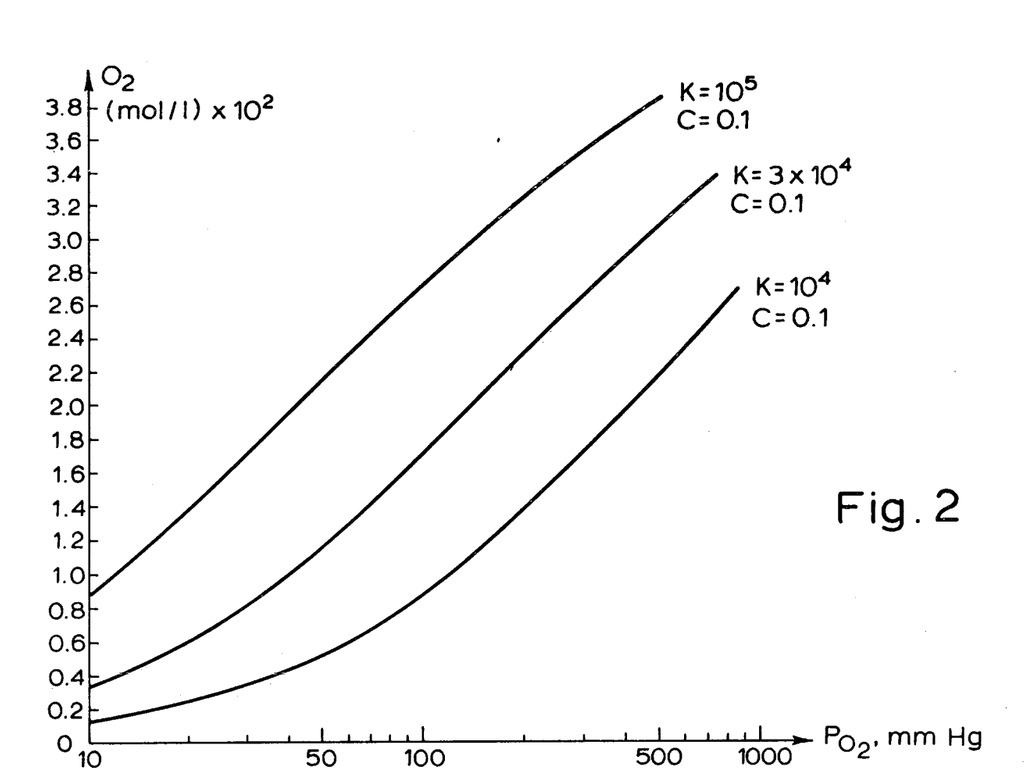
FIG. 2 is a logarithmic plot of the oxygen content of reference liquids according to the invention as a function of the partial pressure of oxygen.

FIG. 2 shows, as a single logarithmical plot, the concentration of total oxygen amount as function of the partial pressure of oxygen for oxygen complexes with the three above-mentioned stability constants, each of them in a concentration of $10^{-1}$ mol/liter in the reference liquid. It will be seen how the oxygen complex compounds show a considerable oxygen buffer capacity (considerably greater steepness of the graph than for H₂O) in a broad range around the partial pressures mentioned, so that loss or gain of a certain amount of oxygen in the range stated will result in percent-wise the same (relatively small) change in the oxygen partial pressure of the system.

On the background of the examples given above and FIG. 2 it can be stated that also for complex compounds binding oxygen according to the reaction scheme $$2L + O_2 \rightarrow L - O_2 - L,$$

beneficial stability constants will be in the range of $10^3$–$10^{5.5}$, especially $10^4$–$10^5$.

When the reference liquid according to the invention contains, as oxygen buffer capacity-increasing organic substance, an oxygen complex-forming compound, the concentration of this compound is preferably between $10^{-4}$ and 1 mol per liter, especially from $10^{-3}$ to $5 \cdot 10^{-1}$ mol per liter.

Figure 3:
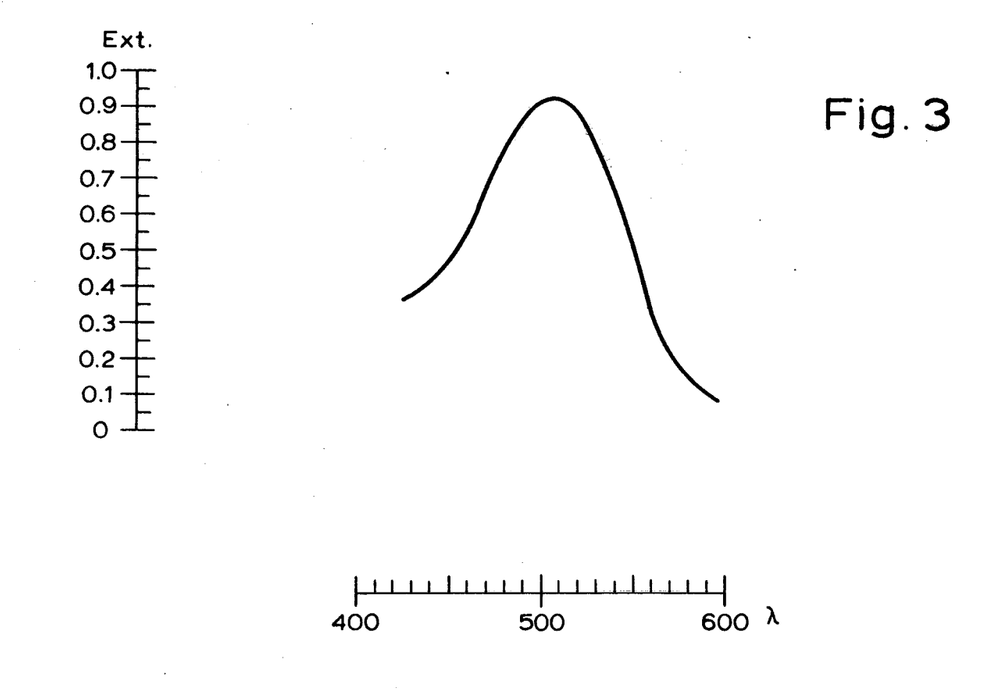
FIG. 3 is a curve showing the absorption of the dyestuff Ponseau 4R.

When the reference liquid according to the invention contains a coloring component which is to "simulate" hemoglobin and permit the use of the reference liquid for quality control and/or calibration of the hemoglobin measuring part of the blood measuring equipment, the coloring component is preferably one having an absorption maximum at or around an isobestic point of the system hemoglobin/hemoglobin-oxygen-complex (in other words, to use the symbols used above, Hb/HbO₂), i.e. the point in which the molar extinction caused by Hb has the same size as the molar extinction caused by HbO₂, as blood gas measuring equipment comprising a hemoglobin measuring part is usually equipped with such filters that the absorption of the sample introduced is measured at or in a narrow range around one of the isobestic points, e.g. the point at 505 nm. Hence, dyestuffs having absorption maximum around 500 nm are suitable for use in the reference liquid according to the invention. As examples of such dyestuffs may be mentioned Amaranth, Allura Red and Ponceau 4 R, 70%. The last-mentioned dyestuff is a chemical azo dyestuff, having C.I. No. 16,255 (1956). The compound is the trisodium salt of 1-(4-sulfo-1-naphthyl-azo)-2-naphthol-6,8-disulfonic acid. The dyestuff used should suitably be contained in the liquid in such concentration that it corresponds to the extinction of human blood, which, for Ponceau 4 R, 70% means a concentration of about 1.7 g/liter. FIG. 3 shows the absorption curve of Ponceau 4 R. When the reference liquid according to the invention is in the form of a dispersion, the coloring component may also be dissolved in the disperse phase, which makes the reference liquid resemble blood. Suitable dyestuffs for this purpose are, for example Grasol Fast Red BR from Ciba-Geigy and Sudan Rot 7B from BASF; these two dyestuffs are soluble in silicon oil.

A special aspect of the present invention relates to a liquid for use as a reference liquid or as a starting material for the preparation of a reference liquid, the oxygen buffer system of which liquid consisting fully or partially of polymer-coated microcapsules containing at least one organic substance having a considerably greater ability to reversibly contain oxygen than has water. In its broadest aspect, as a reference liquid for quality control and/or calibration of apparatus for measurement of $P_{O_2}$ (or as a starting material for the preparation of such reference liquid), the said liquid, hence, is characterized in that it contains an aqueous phase and, suspended in the said aqueous phase, polymer-coated microcapsules containing at least one organic substance which shows considerably greater ability to reversibly contain oxygen than does water. In accordance with what is explained below, this reference liquid will be able to show, at a fixed temperature, a known pH, a known partial pressure of carbon dioxide and a known partial pressure of oxygen, when its water phase contains at least one pH buffer system, and preferably, its water phase, as explained below, contains both a hydrogen carbonate ion-carbon dioxide-pH buffer system and an additional pH buffer system, which additional pH buffer system is preferably a phosphate buffer system.

The organic substance which is contained in the microcapsules may be any of the above-mentioned oxygen buffer capacity-increasing substances, in other words, organic substances showing a considerably greater ability to reversibly contain oxygen than does water.

In accordance with a preferred aspect of the present invention, the polymer-coated oxygen carriers which are present in the form of microcapsules, are selected according to the criteria stated above in connection with suspended or emulsified oxygen carriers.

As preferred organic substances which may be contained in the microcapsules may be mentioned hydrocarbons, fluorocarbon compounds, esters (e.g. dibutyl phthalate) and silicon oils, and it is especially preferred that the microcapsules contain isooctane or perfluorotributyl amine or, what is especially preferred, a mixture of isooctane and perfluorotributyl amine. When the microcapsules contain a mixture of isooctane and perfluorotributyl amine, it is, in accordance with the invention, especially preferred that the volume ratio between isooctane and perfluorotributyl amine is 5-9:4-10, especially 7–8:3–2, and it is especially highly preferred that the volume ratio is about 3:1, as this gives the optimum density of the mixture.

The polymer coating of the microcapsules may be any polymer which can be formed in situ at the interface between an organic phase and an aqueous phase, either by interface polymerization or by interface precipitation. As examples of materials which may be formed by interface polymerization may be mentioned proteins, polyamides (nylon), polyurethane, polyurea, polysulphonamide or polyphenyl esters, and as examples of polymer materials which may be precipitated in the interface may be mentioned cellulose nitrate, protein, polystyrene and "silastic" (which latter, however, requires a subsequent vulcanisation). According to the invention it is preferred that the polymer coating of the microcapsules is a non-biological and non-proteinaceous material, especially nylon formed in situ.

The size of the microcapsules is preferably of the order of $1-5\mu$, and the polymer coating is preferably of the order of 300–600 Ångström.

By including the oxygen buffer capacity-increasing substance in a polymer coating in the form of microcapsules, there is obtained firstly a more stable suspension than through emulsification of the same substances, and secondly, there is obtained the advantage that oxygen buffer capacity-increasing substances which would otherwise present problems because of their aggressivity towards parts of the blood gas measuring apparatus, for example the polypropylene membranes of the oxygen electrodes, may be used in the reference liquid substantially without any problems. Furthermore, by using the microcapsules, it becomes possible to combine several substances in the organic phase in such a way that its density becomes equal to or very close to the density of water which counteracts any tendency for the disperse phase to separate from the aqueous phase, and the combination of several substances can also contribute to improve other properties, for example the strength and smoothness of the polymer membrane around the microcapsules. Thus, for example, addition of carbon tetrachloride to isooctane encapsulated in nylon contributes to increase the smoothness of the nylon membranes and to reduce the tendency of the microparticles to agglomerate.

The preparation of a suspension of microcapsules of the above-described kind is performed by suspending at least one organic substance which shows considerably greater ability to reversibly contain oxygen than does water, in an aqueous phase under such conditions that the single suspended particles are coated with a polymer material. A technique which, in certain respects, resembles this process is described in the literature ("Semipermeable Aqueous Microcapsules", T. M. S. Chang, F. C. MacIntosh, S. G. Mason, Can. J. of Physiology and Pharmacology 44, 115–128 (1966), "Artificial Cells", Thomas Ming Swi Chang, Charles C. Thomas, Springfield, Ill., U.S.A. 1972). In these articles, methods are disclosed for the preparation of thin, stable polymer membranes around aqueous microdrops, either through interface polymerisation or through interface precipitation. The enclosed aqueous phase could contain enzymes and/or other proteins and was separated from a continuous aqueous phase by means of the semipermeable membranes formed. In the above-mentioned works, the two thus separated aqueous phases were to serve as a model for biological cell walls. By means of such a model, the study of the single cell functions were facilitated. This required a semipermeable membrane between two aqueous phases so that exchange of water, salts and small molecules could take place, whereas large molecules (e.g. enzymes) were retained. The preparation of the polymer membranes around the aqueous microdrops in this known art was performed in the following manner:

(1) The aqueous protein solution (possibly containing organic diamine) was emulsified in an organic liquid by means of a suitable soap.

(2) By addition of a suitable material to the continuous phase, a polymer membrane was formed around each droplet. The membrane formation was performed either by interface polymerisation, in other words a chemical process, or by interface precipitation, in other words a physical process, dependent on the lower solubility for a polymer in the interface.

(3) By means of suitable solvents and/or surface active agents, the microcapsules formed were removed from the organic phase and suspended in an aqueous medium. In a specific example, the already previously investigated interface polymerisation (Morgan and Kwolek, J. Pol. Sci. 40, 299, 1959) between a water soluble aliphatic diamine and a solution of a dicarboxylic acid chloride in an organic solvent was utilized. Chang et al. showed that polymerisation also took place when the water phase was present finely divided in the organic phase.

In contrast to the above known art, the coating according to the present invention aims at a stabilisation of a disperse organic phase in an aqueous medium and a reduction of the diffusion rate of the liquid phases through the membrane, and a characteristic difference in comparison with the method according to Chang et al. is that in the process of this invention, an organic phase, rather than the water phase, is finely divided.

In preferred embodiments of the process according to this invention, the polymeric coating material is formed by interface polymerisation between polymer-forming components, one of which being present in the organic phase, and the other one being present in the aqueous phase. For example, in accordance with a preferred embodiment, nylon is formed in the interface in that the organic phase contains a sebacoyl chloride and the aqueous phase contains hexanediamine.

The organic phase may be suspended in the aqueous phase in any suitable way, but according to the invention it is preferred that the organic phase is suspended in the aqueous phase by being sprayed into the aqueous phase by means of a nozzle. Thus, for example, microcapsules of encapsulated isooctane suspended in an aqueous phase may be prepared by spraying, through a nozzle, isooctane having a content of 10% sebacoyl chloride in an aqueous solution containing hexanediamine and an emulsifier, for example, FC-128, which is the potassium salt of fluorinated alkyl carboxylate from 3M Company. For example, per 5 liters of aqueous solution containing 0.1 kg 1,6-hexanediamine and 1.5 g FC-128, there may be introduced, by spraying, 100–500 ml isooctane containing 10% sebacoyl chloride. After the addition of spraying, it is suitable to stir, for example, to slowly stir for about 1 hour, in order to secure that the reaction is completed. Thereafter, the resulting suspension may be allowed to stand until the particles have collected in a top phase, and the lower phase consisting of water, diamine and soap may be withdrawn for regeneration. Thereafter, the top phase is suitably washed 3–5 times with deionized water and thereafter 2-3 times with aqueous phosphate-bicarbonate buffer which constitutes the continuous phase in the final suspension. Subsequent to the last separation which may be facilitated by means of mild centrifugation, one has a suspension which is suitable for synthesizing a reference liquid through equilibration with a gas mixture having a known partial pressure of $CO_2$ and a known partial pressure of $O_2$.

When the organic phase which is to be enclosed in microcapsules comprises two organic components which are not mutually soluble, the preparation of the microcapsules according to the invention is performed by suspending one organic component in the other through spraying the first-mentioned component into the second component through a nozzle, and thereafter suspending the resulting suspension in the aqueous phase by spraying it into the aqueous phase through a nozzle. In this way, for example, a suspension of microcapsules, each of which contains perfluorotributyl amine suspended in isooctane, may be prepared.

Now, the especially characterizing features of the reference liquid according to the invention, viz. the oxygen buffer system and the optional hemoglobin-simulating coloring agent have been explained. In the following, the more conventional properties of the reference liquid, i.e. its pH buffer properties and its $P_{CO_2}$ buffer properties will be dealt with.

The establishment of suitable pH and $P_{CO_2}$ buffer mixtures pertains to the known art. In principle, one may, in establishing such buffer solutions, utilize the well-known relationship between carbon dioxide dissolved in water and the pH of the solution:

$$pH = pK_A - m\sqrt{\mu} + \log \cdot \frac{[HCO_3^-]}{[CO_2]} \text{ (a modified Henderson-Hasselbalch equation)}$$

wherein $pK_A$ is the thermodynamic dissociation exponent of carbonic acid, m is a constant, $\mu$ is the ionic strength, $[HCO_3^-]$ is the molar concentration of hydrogen carbonate ion, and $[CO_2]$ is the molar concentration of carbon dioxide.

It will thus be seen that the pH of a hydrogen carbonate/carbon dioxide solution is defined and known when the hydrogen carbonate and carbon dioxide concentrations are known. Such systems containing known concentrations of hydrogen carbonate ion and carbon dioxide may be established in various manners, e.g. by equilibrating a sodium hydrogen carbonate solution with a $CO_2$-containing gas of known partial pressure of $CO_2$, but it is also possible to start from sodium carbonate and form sodium hydrogen carbonate in situ by "titration" with the carbon dioxide, and likewise, it is possible to establish a solution with known hydrogen carbonate ion concentration and known carbon dioxide concentration by adding an acid, such as HCl, to a hydrogen carbonate solution or a carbonate solution. These various procedures and the corresponding calculations of the parameters of the established systems are dealt with in more detail below.

The partial pressure of carbon dioxide in a liquid depends on the concentration of dissolved carbon dioxide in the liquid and of the solubility of carbon dioxide in the liquid in question, in the following manner:

$$[CO_2]_t = k_t \cdot P_{CO_2}$$

wherein $k_t$ is representative of the solubility of carbon dioxide in the liquid, which solubility is temperature-dependent. A liquid containing a hydrogen carbonate ion-carbon dioxide buffer system (as shown by the above Henderson-Hasselbalch equation) will, hence, show a fixed $P_{CO_2}$ at fixed pH.

For the purpose of the present invention, where it is desirable that the reference liquid retains, to the degree possible, its declared values for pH and $P_{CO_2}$ during storing and manipulation, it is desirable to take measures to secure, to the degree possible, that gain or loss of small amounts of carbon dioxide (during storing and/or manipulation) results in as little change in pH and $P_{CO_2}$ as possible, and according to the invention, this is suitably obtained by combining the hydrogen carbonate ion-carbon dioxide buffer system with another pH buffer system, according to the invention suitably a phosphate buffer system. Through this, the total buffer effect is increased with respect to the variation of both pH and $P_{CO_2}$ at loss or gain of small amounts of carbon dioxide. Hence, preferred reference liquids according to the invention contain both a phosphate buffer system and a hydrogen carbonate ion-carbon dioxide buffer system. In analogy with the above explanation, the establishment of these systems may be obtained in various manners, e.g. by equilibration of a phosphate buffer system with carbon dioxide, by equilibration of a phosphate/carbonate buffer system with $CO_2$, by addition of an acid, for example HCl, to a phosphate/hydrogen carbonate buffer system, or by addition of such an acid to a phosphate/carbonate buffer system. These various methods for establishing such buffer systems also pertain to the known art, but will, however, be discussed in greater detail below.

As most of the parameters with respect to which the reference liquid according to the invention is to be used for quality control and/or calibration, are temperature-dependent, the quality control and/or calibration should be performed at a specific temperature for which the reference liquid is adapted, and the packaging of the reference liquid should state at which temperature or in which temperature range the declared parameter values apply and/or can be guaranteed with a particular uncertainty. In connection with the below explanation of the preparation of the reference liquid it will be understood that one may either prepare and pack the reference liquid at the same temperature as the one at which it is later to be used, or one may prepare and pack the reference liquid at a temperature different from the use temperature and then, by means of physical-chemical calculations and/or empirical corrections, determine the parameter values declared for the use temperature on the basis of the parameter values applying at the preparation temperature.

As mentioned above, the reference liquid according to the present invention must be enclosed in a gas-tight container, and according to the invention it is desirable that the reference liquid is enclosed substantially free of gas phase in the gas-tight container. The reason for this is that a possible difference between the temperature at which the declared data of the reference liquid apply, and the temperature at which the container with the reference liquid is opened or punctured for introduction of the reference liquid into the equipment to be checked or calibrated, will result in less changes in the parameters measured on the reference liquid at the measuring temperature in the cases where the reference liquid is enclosed in its container substantially free of gas phase, than in the cases where there is a substantial gas phase present together with the reference liquid in the gas-tight container.

In practice, the packing of the reference liquid in the gas-tight container will be performed under scrupulously controlled conditions with respect to temperature and pressure, and it is important that the container is totally filled up with liquid. Suitably, the container is to a certain extent flexible so that there will be no separation of a gas phase (micro-bubbles) at varying barometer pressure and temperature during storing, and suitably, the reference liquid filled into the container shows a reduced total gas pressure, in order to secure that at varying temperature conditions during storing, transportation or at the use, e.g. at temperatures between 0° and 50° C., no formation of micro-bubbles due to supersaturation of dissolved gas will take place.

Suitable containers for packing the reference liquid according to the invention are, e.g. ampoules, cannulla-ampoules, tubules (glass cylinders closed at both ends with metallized plastic or rubber stoppers), metal capsules, vials, and preferably tubes with sealed tip or metal foil tubes. The container should be chemically inert to the reference liquid, in order to avoid any changes in the parameters of the reference liquid due to reactions between the components of the reference liquid and the container material. Hence, if the container is of metal, it will be suitable that it is lined with a material which shields the metal from the reference liquid, for example with a plastic foil such as a polyethylene foil.

Hence, a suitable embodiment of the container is for example a continuous metal and plastic foil container which may be of the shape corresponding to the known coffee bags, milk cartons (tetrapacks), and shampoo pads, or preferably a plastic-laminated metal tube closed at both ends by welding together the plast foil. Here, it is essential that the materials and design of the container are so selected that the diffusion through the welding seams is so small that loss of $O_2$ and $CO_2$ during storing, e.g. during two years of storing time, will not change the liquid beyond what is acceptable; for most practical utilities, changes of $P_{CO2}$ and $P_{O2}$ of at the most about 2%, preferably at the most about 1%, will be acceptable. Furthermore, it is important that the specific material and thickness of the plastic foil are so selected that the amount of $CO_2$ and $O_2$ absorbed in the plastic foil will not influence the measuring results, e.g. presuming that the containers are filled at 37° C. and opened or punctured at about 20° C.

A plastic laminated metal tube of the above kind may be example comprise an interior layer of for example 50$\mu$ of polyethylene or Barex TM 210 (PAN C, polyacrylonitrile copolymer) (Lonza), which is used because of its welding properties (in this case, the tube may be closed by periphery welding). If it is desired to be able to heat-sterilize the reference liquid, polypropylene may be used instead of the above-mentioned material. The metal may suitably be aluminum foil which is diffusion tight. A suitable thickness for the aluminum foil is for example 30$\mu$, which is greater than the thicknesses in which aluminum foil is usually employed; the purpose of using the greater thickness is to reduce the risk of "pin holes". Another possibility is to use several thinner aluminum foils laminated together. If desired, a layer of nylon may be incorporated between the polyethylene and the aluminum foil, for example a nylon layer of 15$\mu$, for increasing the strength of the packing, and the exterior layer may be nylon in a thickness of suitably about 12$\mu$, or polyester in the same thickness.

Naturally, the container should be designed in such a manner that the reference liquid may be introduced in a blood gas measuring equipment anaerobically, i.e. without access for atmospheric air, and the known art comprises various suitable designs and adaptors.

The exact process selected in the preparation of the reference liquid will depend on the identity of the systems involved in the reference liquid and, for example, on the method selected for establishing the pH system, vide the above explanations. When the oxygen buffer capacity-increasing organic substance is a non-water soluble organic substance showing great solubility for oxygen, and the adjustment of the pH-$P_{CO2}$ system is performed by equilibration of a buffer system with $CO_2$, a suitable process may for example be one in which the chemicals forming part of the buffer system or systems are weighed out exactly and dissolved in an exactly measured amount of deionized water, the water phase and the organic phase are mixed and emulsified in the desired weight ratio, a very fine emulsion being aimed at, e.g. with an emulsifying level down to between $10^{-1}\mu$ and $10^{-2}\mu$, if necessary using a suitable emulsifier, the resulting emulsion is transferred to an equilibration tank, suitably a thermostated tank with stirrer and gas jets, the total volume of the tank being suitably 50-100% larger than the volume of the liquid to be equilibrated, said thermostating being performed at suitably 37° C.$\pm$0.1° C., and stirring and gas dosing may be performed in a manner so as to ensure a relatively fast equilibration, e.g. an equilibration time of at least 16 hours (overnight), the equilibration is performed with a gas mixture of exactly adjusted and known partial pressure of $CO_2$ and $O_2$, which gas mixture is suitably prepared in a manner known per se using a $CO_2$ gas supply, an $O_2$ gas supply, an $N_2$ gas supply, a pre-moistener and a pressure regulating unit, whereby, e.g. for the equilibration, in the course of 16 hours, of 200 liters of reference liquid which does not in advance contain $CO_2$, and with an average utilization of 2% of the gas mixture, there is suitably used a gas flow of about 120 liters/minute, and whereby continuous monitoring of the partial pressure of $CO_2$ and $O_2$ in the gas mixture is performed by means of $P_{CO2}/P_{O2}$ electrodes which may be controlled by means of a reference gas measuring equipment, the thus equilibrated reference liquid is filled anaerobically and substantially free of gas phase into the containers, and optionally, sterilization is performed in a manner known per se, e.g. by radioactive irradiation. If addition of acid is used instead of the equilibration with carbon dioxide for establishing $P_{CO2}$, such as mentioned above, this addition of acid is suitably performed after the equilibration with $O_2$.

The reference liquids prepared and packed in this manner should be carefully checked by taking out samples at suitable intervals and measuring these samples by means of $P_{CO2}/P_{O2}$ measuring apparatus, pH equipment, Hb equipment, and total $CO_2/O_2$ measuring equipment, the check on total $CO_2/O_2$ being performed to secure that the $CO_2/O_2$ capacity is in fact present. Officially recognized reference preparations and procedures may be used for the calibration of the measuring equipment in connection with this checking, like in connection with the fine adjustment of the production parameters.

When the reference liquid according to the invention is used for quality control, it is, as indicated above, introduced substantially anaerobically into the blood gas measuring equipment, preferably in the same manner and under the same conditions as the blood samples for which the blood gas measuring equipment is designed, the prescriptions given on the packing of the reference liquid being, naturally, carefully adhered to, and the reference liquid passes into the measuring units comprised by the blood gas measuring equipment, usually measuring electrodes and, with respect to the possible hemoglobin unit, usually a photometer. The response of the measuring units on the reference liquid is recorded, and if the recorded values deviate to an unacceptable degree from the declared values of the reference liquid, the problems must be analysed in order to ascertain and remedy errors in the blood gas measuring equipment and/or its calibration liquids and/or the procedure for operating the blood gas measuring equipment.

When the reference liquid according to the invention is used for calibrating blood gas measuring equipment, it is introduced anaerobically into the measuring units of the blood gas measuring equipment, whereby the prescriptions given on the packing of the reference liquid are naturally carefully adhered to, and the measuring equipment is adjusted until there is conformity between the values read from the blood gas measuring equipment and the values declared on the reference liquid. In using the principle of the present invention for calibration, the most suitably way will be to calibrate the blood gas measuring equipment with two different reference liquids according to the invention with values differing from each other, this being quite in conformity with known art, and like the above-mentioned Radiometer ABL1 equipment, the blood gas measuring equipment will be adapted to automatically perform such a calibration, in this case using pre-fabricated and pre-packed reference liquids according to the invention instead of the known art reference liquids which are made ready for use in the apparatus proper.

Now follow firstly specific prescriptions for establishing the pH/$P_{CO_2}$ system, and thereafter working examples illustrating the reference liquid according to the invention. It will be understood that although a very great exactitude in the parameters of the reference liquid may be obtained already on the basis of the calculations stated in the below prescriptions, using the empirical constants stated, the utmost exactitude of the parameters will depend on a fine adjustment performed in the particular production equipment and based upon partly empirical constants characteristic to the equipment, and partly corrections after control measurements against for example officially acknowledged standards.

PRESCRIPTION 1.

In a buffer system consisting of sodium hydrogen carbonate equilibrated to known partial pressure of $CO_2$, the pH can be calculated according to the Henderson-Hasselbalch equation:

$$pH = pK_A + \log \cdot \frac{[HCO_3^-]_a}{[CO_2]_a}$$

$pK_A$ is the thermodynamic dissociation exponent. To calculate the pH, it is necessary to correct $pK_A$ for the effect of ionic strength. This is done according to the Debye-Huckel limiting law for activity coefficients. The law is used in approximated form:

$$pK_A' = pK_A - 0.495\sqrt{\mu}$$

wherein $\mu$ is the ionic strength of the electrolytes in the solution, and 0.495 is an empirically ascertained constant. In connection with the introduction of molar concentrations of [$HCO_3^-$] and [$CO_2$], the Henderson-Hasselbalch equation becomes as follows:

$$pH = pK_A - 0.495\sqrt{\mu} + \log [HCO_3^-] - \log [CO_2]$$

[$CO_2$] is found from the equation:

$$[CO_2] = \alpha \cdot P_{CO_2} \cdot 10^{-3}$$

$\alpha$ is the modified Bunsen absorption coefficient.

The pH in a $24 \cdot 10^{-3}$ M solution of sodium hydrogen carbonate equilibrated with a gas mixture with a partial pressure of $CO_2$ of 40 mm Hg will be 7.53. If indifferent salt (e.g. NaCl) is added to a total ionic strength of 0.21, the pH will be 7.38.

The following constants, valid at 37° C., are used:

$$pK_A = 6.33$$

$$\alpha = 0.032$$

The prescription applies at 37° C.

The pH in a $12 \cdot 10^{-3}$ M solution of sodium hydrogen carbonate equilibrated with a gas mixture with a partial pressure of $CO_2$ of 80 mm Hg will be 6.95.

If indifferent salt (e.g. NaCl) is added to a total ionic strength of 0.11, the pH will be 6.84.

The same constants as above are used.

PRESCRIPTION 2.

When a phosphate buffer is equilibrated with $CO_2$, the pH of the buffer is changed in dependence of the amount of $CO_2$. In a phosphate-hydrogen carbonate-mixture system, the following equation will establish itself:

If the initial concentrations of $HCO_3^-$, $H_2PO_4^-$ and $HPO_4^{--}$, respectively, are designated:

A, B, C the result, after mixing, is $$(A-a)+(B-a)\rightleftarrows(C+a)+a$$

wherein a is the change which will bring the system into equilibrium. When carbon dioxide is added until the pressure corresponding to the concentration m, another change results:

$$(A-\alpha)+(B-\alpha)\rightleftarrows(C+\alpha)+m$$

The mass action equation for the hydrogen carbonate system is:

$$\frac{[H^+](A-\alpha)}{m} = K_1$$

and for the phosphate system:

$$\frac{[H^+](C+\alpha)}{(B-\alpha)} = K_2$$

Elimination of $\alpha$ from the equations results in:

$$\frac{([H^+] \cdot A) - (K_1 \cdot m)}{[H^+]} = \frac{(K_2 \cdot B) - ([H^+] \cdot C)}{[H^+] + K_2}$$

This results in a second degree polynomium with respect to [H+], and the pH can be calculated:

$$pH = -\log\left(\frac{K_1 \cdot m + K_2 \cdot B - K_2 \cdot A \,^{(\pm)} \sqrt{(K_1 \cdot m + K_2 \cdot B - K_2 \cdot A)^2 + D}}{2(C+A)}\right)$$

$D = 4(C+A)K_1 \cdot K_2 \cdot m$ $K_1$ is the first acid strength constant of carbonic acid.
$K_2$ is the second acid strength constant of phosphoric acid.
A is molar concentration of hydrogen carbonate.
B is molar concentration of dihydrogen phosphate.
C is molar concentration of monohydrogen phosphate.
In the calculations, the following constants are used:

$pK_1 = 6.328 - 0.495\sqrt{\mu}$ (valid at 37° C.)

$pK_2 = 7.029 - 0.495\sqrt{\mu}$ (valid at 37° C.)

In a phosphate buffer wherein C=B, $\mu$=0.1, and the partial pressure of $CO_2$ is 40 mm Hg, pH will be 6.59. C=B=0.025 mol/liter.

In a phosphate buffer wherein C=4 B, and $\mu$=0.17, and the partial pressure of $CO_2$ is 80 mm Hg, the pH will be 6.90. C=0.0523 and B=0.0131 mol/liter.

In both solutions, the initial concentration of hydrogen carbonate =0.

PRESCRIPTION 3.

By adding hydrogen carbonate to the phosphate buffer solutions according to prescription 2, pH can be varied.

A buffer consisting of C=B=0.022 M, and A=0.012 M, equilibrated with a gas mixture with a partial pressure of $CO_2$ of 80 mm Hg, has pH 6.84 ($\mu$=0.1).

A buffer consisting of C=0.047 M, B=0.012 M, and A=0.022 M, equilibrated with a gas mixture having a partial pressure of $CO_2$ of 40 mm Hg, has pH 7.36 ($\mu$=0.17).

PRESCRIPTION 4.

The sodium hydrogen carbonate in the above prescriptions may be formed by titration of sodium carbonate with carbon dioxide.

In this case,

At pH 7, the equilibrium is displaced completely to the right, as less than 0.1% of the carbonate is unconverted.

Hence, in prescription 3, the hydrogen carbonate may be replaced with carbonate in half of the concentration to result in the same pH as calculated in prescription 3.

PRESCRIPTION 5.

Prescription 1 may be calculated with carbonate instead of hydrogen carbonate. Carbonate is to be used in half of the concentration, cf. the reaction equilibrium in prescription 4.

PRESCRIPTION 6.

Hydrogen carbonate buffer+acid, e.g. HCl

When the hydrogen carbonate buffer is not prepared by equilibration with carbon dioxide, it may, for example, be prepared by addition of hydrogen ion from, e.g., hydrochloric acid, to a hydrogen carbonate solution.

Hence, in prescription 1, 80 mm Hg of $P_{CO_2}$ corresponds to $2.56 \times 10^{-3}$ mol of $CO_2$ per liter, which may be formed from hydrogen carbonate ion by addition of acid.

$HCO_3^- + H^+ = CO_2 + H_2O$

To form $2.56 \times 10^{-3}$ mol, $2.56 \times 10^{-3}$ mole of H+ are required, for example in the form of HCl.

This means that $(12 \times 2.56) \times 10^{-3} = 14.56 \times 10^{-3}$ mol of hydrogen carbonate to which are added $2.56 \times 10^{-3}$ mol of HCl and sodium chloride to a total ionic strength of 0.11 gives, in 1 liter of solution, a pH of 6.84.

When it is desired to prepare the liquid on the basis of carbonate, the following applies:

1 liter of solution containing $(12+2.56) \times 10^{-3}$ mol of carbonate $\times 14.56 \times 10^{-3}$ mol, to which are added $(14.56+2.56) \times 10^{-3}$ mol $= 17.12 \times 10^{-3}$ mol of hydrogen ion in the form of hydrochloric acid, and sodium chloride to a total ionic strength of 0.11, also results in pH 6.84.

PRESCRIPTION 7.

When the buffers mentioned in prescription 3 are prepared by addition of acid in a closed container, a buffer containing C=B=0.022 and A=$14.56 \times 10^{-3}$ mol/liter admixed with $2.56 \times 10^{-3}$ HCl per liter has pH 6.84, and the ionic strength in this solution becomes 0.1025.

When the buffer is prepared from sodium carbonate, the same amount of sodium carbonate is added, while the amount of acid is increased to $(14.56+2.56) \times 10^{-3} = 17.12 \times 10^{-3}$ mol of HCl per liter.

A buffer consisting of C=B=0.022 and sodium carbonate=$14.56 \times 10^{-3}$ mol/liter admixed with $17.12 \times 10^{-3}$ mol of HCl per liter will show a pH of 6.83, as the ionic strength in this solution is increased to 0.117.

EXAMPLE 1.

Bicarbonate-containing phosphate buffer with a disperse phase of fluorohydrocarbon.
The composition is:

| In the water phase: | |
|---|---|
| disodium hydrogen phosphate | 0.047 molal |
| potassium dihydrogen phosphate | 0.012 molal |
| sodium hydrogen carbonate | 0.022 molal |
| Ponceau 4 R | 1.7 g/liter |

The water phase constituted 60% of the liquid, 40% being fluorohydrocarbon (perfluorotributyl amine) emulsified in the water phase.

This liquid is suitable for synthesizing a reference liquid having pH=7.36, $P_{CO_2}$=40 mm Hg, $P_{O_2}$=70 mm Hg, and Hb=14 g%, at 37° C., which is done by equilibrating the liquid with a gas mixture having a partial pressure of $CO_2$ of 40 mm Hg and a partial pressure of $O_2$ of 70 mm Hg at a temperature of 37° C.

EXAMPLE 2.

A bicarbonate-containing phosphate buffer with a disperse phase of fluorohydrocarbon.
The composition is:

| In the water phase: | |
|---|---|
| disodium hydrogen phosphate | 0.022 molal |
| potassium dihydrogen phosphate | 0.022 molal |
| sodium hydrogen carbonate | 0.012 molal |
| Ponceau 4 R | 1.7 g/liter |

The water phase constitutes 60% of the liquid, 40% being fluorohydrocarbon (perfluoromethyl cyclohexane) emulsified in the water phase.

This liquid is suitable for synthesizing a reference liquid having pH=6.84, $P_{CO_2}$=80 mm Hg, $P_{O_2}$=150 mm Hg, and Hb=14 g%, at 37° C., which is done by equilibrating the liquid with a gas mixture having a partial pressure of $CO_2$ of 80 mm Hg and a partial pressure of $O_2$ of 150 mm Hg at a temperature of 37° C.

EXAMPLE 3

A bicarbonate-containing aqueous phosphate buffer solution having a content of iron-phthalocyanine tetrasulfonic acid.
The composition is:

| | |
|---|---|
| disodium hydrogen phosphate | 0.022 molal |
| potassium dihydrogen phosphate | 0.022 molal |
| sodium hydrogen carbonate | 0.012 molal |
| iron(II) phthalocyanine tetrasulfonic acid | 2% |
| iron(II) phthalocyanine tetrasulfonic acid ($O_2$ complex) | 1% |

This solution is suitable for synthesizing a reference liquid having pH=6.84, $P_{CO_2}$=80 mm Hg, $P_{O_2}$=1 mm Hg, and Hb=0 g%, at 37° C., which is done by equilibrating the solution with a gas mixture having a partial pressure of $CO_2$ of 80 mm Hg and a partial pressure of $O_2$ of 1 mm Hg at a temperature of 37° C.

EXAMPLE 4

A bicarbonate-containing phosphate buffer having a disperse phase of silicone rubber.
The composition is:

| In the water phase: | |
|---|---|
| disodium hydrogen phosphate | 0.047 molal |
| potassium dihydrogen phosphate | 0.012 molal |
| sodium hydrogen carbonate | 0.021 molal |
| Ponceau 4 R | 1.7 g/liter |

The water constituted 60% of the liquid, the remaining 40% being finely dispersed silicone rubber particles (CAF4/60 "RHODORSIL").

This liquid is suitable for synthesizing a reference liquid having pH=7.36, $P_{CO_2}$=40 mm Hg, $P_{O_2}$=70 mm Hg, and Hb=14 g%, at 37° C., which is done by equilibrating the liquid with a gas mixture having a $CO_2$ partial pressure of 40 mm Hg and an $O_2$ partial pressure of 70 mm Hg at 37° C.

In each of the above examples, one may, instead of the equilibration with $CO_2$, perform the addition of an acid, for example HCl, according to the prescriptions 6 and 7.

EXAMPLE 5

A bicarbonate-containing phosphate buffer having a disperse phase of nylon-coated microparticles of silicone oil.

The composition is:

| In the water phase: | |
|---|---|
| disodium hydrogen phosphate | 0.047 molal |
| potassium dihydrogen phosphate | 0.012 molal |
| sodium hydrogen carbonate | 0.022 molal |
| Ponceau 4 R | 1.7 g/liter |

The water phase constitutes 60% of the liquid, the remaining 40% being fluorohydrocarbon (perfluorotributyl amine) emulsified in the water phase.

The organic phase: microcapsules of silicone oil coated with nylon.

Preparation as follows:

1.6 g sebacoyl chloride is dissolved in 80 ml of dimethyl siloxan polymer 200 fluid/100 from Dow Corning. 200 is the type, 100 is the viscosity in centistokes. 35 ml of the mixture is, at a pressure of about 110 atm., sprayed, through a nozzle, into 400 ml of aqueous solution containing 3 g NaOH, 4 g 1,6-hexanediamine (Fluka) and 15 g Tween ®80 (surface active substance from Merck Schuchardt). The mixture is sprayed into the solution under the water surface. The aqueous solution is vigorously stirred during the spraying and for 4 minutes thereafter. On the surface of the silicone oil particles, sebacoyl chloride reacts with 1,6-hexanediamine in the aqueous phase with formation of a nylon membrane.

The resulting particles are separated by centrifugation and washed several times with the aqueous phase which is introduced as the continuous phase. The resulting reference liquid contains 40% of aqueous phase and 60% of disperse phase and is suitable for synthesizing a reference liquid having the specifications stated in example 1, which is performed by equilibration as mentioned in example 1.

EXAMPLE 6

A bicarbonate-containing phosphate buffer with a disperse phase of porous, air-containing silicone rubber.

The composition is:

| In the water phase: | |
|---|---|
| disodium hydrogen phosphate | 0.047 molal |
| potassium dihydrogen phosphate | 0.012 molal |
| sodium hydrogen carbonate | 0.021 molal |
| Ponceau 4 R | 1.7 g/liter |

The water phase constitutes 60% of the liquid, the remaining 40% being finely divided porous silicon rubber particles (CAF4/60 "Rhodorsil"), prepared by applying superatmospheric pressure during the curing and subsequently, still during the curing, releasing the pressure.

This liquid is suitable for synthesizing a reference liquid (having a pH of 7.36, a $P_{CO_2}$ of 40 mm Hg, a $P_{O_2}$ of 70 mm Hg, and a Hb of 14 g%, all at 37° C.), which is performed by equilibrating the liquid with a gas mixture having a partial pressure of $CO_2$ of 40 mm Hg and a partial pressure of $O_2$ of 70 mm Hg at 37° C.

What we claim is:

1. A synthetic reference liquid for quality control and/or calibration of blood gas measuring equipment, said reference liquid showing, at a fixed temperature, a known pH, $PCO_2$ and $PO_2$ value, said reference liquid comprising an aqueous phase containing at least one pH buffer system and particles suspended in said aqueous phase, the particles being either (1) polymeric oxygen-permeable microcapsules containing at least one organic liquid which shows a considerably greater ability to reversibly contain oxygen than does water, or (2) particles of porous silicone rubber.

2. A reference liquid as claimed in claim 1 in which the aqueous phase contains a hydrogen carbonate ion-carbon dioxide-pH buffer system and a phosphate pH buffer system.

3. A reference liquid as claimed in claim 1 in which the microcapsules contain a hydrocarbon, a fluorocarbon compound, an ester and/or silicon oil.

4. A reference liquid as claimed in claim 3 in which the microcapsules contain isooctane.

5. A reference liquid as claimed in claim 3 in which the microcapsules contain perfluorotributyl amine.

6. A reference liquid as claimed in claim 3 in which the microcapsules contain a mixture of isooctane and perfluorotributyl amine.

7. A reference liquid as claimed in claim 6 in which the ratio, by volume, between isooctane and perfluorotributyl amine in the microcapsules is 7-8:3-2.

8. A reference liquid as claimed in claim 7 in which the volume ratio is about 3:1.

9. A reference liquid according to claim 1 in which the polymeric wall of the microcapsules is nylon.

10. A reference liquid as claimed in claim 1, and further comprising a coloring component showing maximum or significant absorption at about 500 nm.

11. A reference liquid according to claim 1, which is enclosed in a gas-tight container substantially free of gas phase.

12. A reference liquid as claimed in claim 1 in which the suspended microcapsules constitute 40-70% of the total volume.

* * * * *

UNITED STATES PATENT AND TRADEMARK OFFICE
CERTIFICATE OF CORRECTION

PATENT NO. : 4,151,108
DATED : April 24, 1979
INVENTOR(S) : Soren Kai Sorensen et al.

It is certified that error appears in the above-identified patent and that said Letters Patent are hereby corrected as shown below:

The term of this patent subsequent to September 19, 1995 has been disclaimed.

Signed and Sealed this

Twenty-fifth Day of September 1979

[SEAL]

Attest:

LUTRELLE F. PARKER
Attesting Officer  Acting Commissioner of Patents and Trademarks

UNITED STATES PATENT OFFICE
CERTIFICATE OF CORRECTION

Patent No. 4,151,108          Dated April 24, 1979

Inventor(s) Soren Kai Sorensen et al.

It is certified that error appears in the above-identified patent and that said Letters Patent are hereby corrected as shown below:

"The term of this patent subsequent to September 19, 1995 has been disclaimed" should read -- The term of this patent subsequent to September 26, 1995 has been disclaimed --.

THIS CERTIFICATE SUPERSEDES CERTIFICATE OF CORRECTION ISSUED September 25, 1979.

Signed and Sealed this

Twenty-second Day of April 1980

[SEAL]

Attest:

SIDNEY A. DIAMOND

Attesting Officer      Commissioner of Patents and Trademarks

UNITED STATES PATENT OFFICE
CERTIFICATE OF CORRECTION

Patent No. 4,151,108            Dated April 24, 1979

Inventor(s) Soren Kai Sorensen et al

It is certified that error appears in the above-identified patent and that said Letters Patent are hereby corrected as shown below:

Column 2, lines 41-44: "FIG. 1 is a graphical representation showing the molar amount of dissolved oxygen as a function of the partial pressure of oxygen for a number of reference liquids according to the invention;" should read -- FIG. 1 is a semi-logrhythmic plot showing the molar amount of dissolved oxygen as a function of the partial pressure of oxygen for a number of liquid systems; --;

Column 2, line 45: "is a logrhythmic plot" should read -- is a semi-logrhythmic plot --.

Signed and Sealed this

Twenty-ninth Day of April 1980

[SEAL]

Attest:

SIDNEY A. DIAMOND

Attesting Officer      Commissioner of Patents and Trademarks